(12) United States Patent
Blackwell et al.

(10) Patent No.: US 9,403,898 B2
(45) Date of Patent: Aug. 2, 2016

(54) METHOD FOR PURIFYING ALBUMIN

(75) Inventors: Lee Edward Blackwell, Nottingham (GB); Jason Cameron, Nottingham (GB); Phillip Harvey Morton, Nottingham (GB); Steven James Burton, Cambridge (GB); Richard Anthony Dodd, Cambridge (GB); Mark Jonathan Burton, Cambridge (GB)

(73) Assignee: NOVOZYMES BIOPHARMA DK A/S, Bagsvaerd (DK)

( * ) Notice: Subject to any disclaimer, the term of this patent is extended or adjusted under 35 U.S.C. 154(b) by 614 days.

(21) Appl. No.: 13/319,027

(22) PCT Filed: May 7, 2010

(86) PCT No.: PCT/EP2010/056262
§ 371 (c)(1),
(2), (4) Date: Feb. 29, 2012

(87) PCT Pub. No.: WO2010/128142
PCT Pub. Date: Nov. 11, 2010

(65) Prior Publication Data
US 2012/0149873 A1    Jun. 14, 2012

(30) Foreign Application Priority Data
May 7, 2009    (EP) .................... 09159642

(51) Int. Cl.
C07K 1/00    (2006.01)
C07K 14/00    (2006.01)
C07K 16/00    (2006.01)
(Continued)

(52) U.S. Cl.
CPC .............. *C07K 16/00* (2013.01); *C07K 14/765*
(2013.01); *C07K 16/18* (2013.01); *C07K 16/44*
(2013.01); *C07K 2317/41* (2013.01); *C07K
2317/569* (2013.01); *C07K 2317/622* (2013.01);
*C07K 2319/20* (2013.01); *C07K 2319/31*
(2013.01); *C07K 2319/43* (2013.01)

(58) Field of Classification Search
CPC ............. B01D 15/3804; B01D 15/362; B01D 15/363; C07K 14/765; C07K 14/4703; C07K 16/00; C07K 16/1027; C07K 16/18; C07K 16/44; C07K 2317/33; C07K 2317/41; C07K 2317/569; C07K 2317/622; C07K 2317/76; C07K 2319/20; C07K 2319/31
See application file for complete search history.

(56) References Cited

U.S. PATENT DOCUMENTS

2003/0125247 A1    7/2003    Rosen et al.
2005/0186664 A1    8/2005    Rosen et al.
(Continued)

FOREIGN PATENT DOCUMENTS

EP    1544620 A1    6/2005
EP    2022855 A1    2/2009
(Continued)

OTHER PUBLICATIONS

P02768 (last viewed on Apr. 4, 2014).*
(Continued)

*Primary Examiner* — Alexander Kim
(74) *Attorney, Agent, or Firm* — Michael Krenicky

(57) ABSTRACT

An improved method for purifying albumin, a variant or fragment thereof, a fusion protein comprising albumin, a variant or fragment thereof, or a conjugate comprising albumin, a variant or fragment thereof is disclosed.

17 Claims, 5 Drawing Sheets

(51) Int. Cl.
*C07K 14/765* (2006.01)
*C07K 16/18* (2006.01)
*C07K 16/44* (2006.01)

(56) References Cited

U.S. PATENT DOCUMENTS

2008/0247951 A1 10/2008 Koch
2010/0196361 A1 8/2010 Wood

FOREIGN PATENT DOCUMENTS

| WO | 93/15199 A1 | | 8/1993 | |
|---|---|---|---|---|
| WO | WO 96/37515 | * | 11/1996 | ........... C07K 14/765 |
| WO | 97/10887 A1 | | 3/1997 | |
| WO | 00/44772 A2 | | 8/2000 | |
| WO | 01/79271 A1 | | 10/2001 | |
| WO | 02/101021 A2 | | 12/2002 | |
| WO | 03/059934 A2 | | 7/2003 | |
| WO | 03/066078 A1 | | 8/2003 | |
| WO | 03/089614 A2 | | 10/2003 | |
| WO | 2005/061718 A1 | | 7/2005 | |
| WO | WO 2007/099374 | * | 9/2007 | ............... B01J 20/22 |
| WO | 2007/146172 A2 | | 12/2007 | |
| WO | WO 2007/146385 | * | 12/2007 | ............. G01N 33/53 |
| WO | 2008/152140 A2 | | 12/2008 | |
| WO | 2009/019314 A1 | | 2/2009 | |
| WO | 2009/105357 A1 | | 8/2009 | |
| WO | 94/29457 A2 | | 12/2011 | |

OTHER PUBLICATIONS

Neyestani et al., Isolation of alpha-lactalbumin, beta-lactoglobulin, and bovine serum albumin from cow's milk using gel filtration and anion-exchange chromatography including evaluation of their antigenicity., Protein Expr Purif. (2003), vol. 29(2), pp. 202-208.*
Peach et al., Biochim Biophys Acta, vol. 1097, pp. 49-54 (1991).
Gasser et al. Biotech Lett, vol. 29, No. 2, pp. 201-212 (2006).
Girrbach et al, J Biol Chem, vol. 275, pp. 19288-19296 (2000).
Ismaili et al, J Chromatog, vol. 780, pp. 467-474 (2002).
Joosten et al, Micro Cell Fac, vol. 2, No. 30, pp. 2-15 (2003).
Kuroda K et al, Appl Env Microbiol, vol. 74, No. 2, pp. 446-453 (2008).
Lengeler et al, Cell Mol Life Sci, vol. 65, pp. 528-544 (2008).
Lussier et al, Biochim Biophys Ada, vol. 1426, pp. 323-334 (1999).
Maras et al., Glycon J, vol. 16, pp. 99-107 (1999).
Miller et al., Prot Expres Purif, vol. 42, pp. 255-267 (2005).
Needleman et al, J Mol Biol, vol. 48, pp. 443-453 (1970).
Rice et al., Trends Genet, vol. 16, pp. 276-277 (2000).
Strall-Boslinger et al., J Biol Chem, vol. 274, pp. 9068-9075 (1999).
Willer et al., Curr Opin Struc Biol, vol. 13, pp. 621-630 (2003).
Lobbezoo et al, 2009, IBC Bioprocess Int Conference 2009.
Bhikhabhai et al, Amersham Pharmacia Biotech, p. 1 (2000).
Kuwano et al, 1991, J Cell Sciences 98, 131-134.
Xia et al, 2006, J Analytical Sci 22 (4), 393-396 (English Translation attached).

* cited by examiner

SEQUENCE LISTING

```
<160> NUMBER OF SEQ ID NOS: 1

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160
```

```
Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Lys Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

```
Ala Asp Asp Lys Glu Thr Cys Phe Ala Glu Glu Gly Lys Lys Leu Val
            565                 570                575

Ala Ala Ser Gln Ala Ala Leu Gly Leu
            580             585
```

METHOD FOR PURIFYING ALBUMIN

CROSS-REFERENCE TO RELATED APPLICATIONS

This application is a 35 U.S.C. 371 national application of PCT/EP2010/056262 filed May 7, 2010, which claims priority or the benefit under 35 U.S.C. 119 of European application no. 09159642.9 filed May 7, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method for purifying albumin, a variant or fragment thereof, a fusion protein comprising albumin, a variant or fragment thereof, or a conjugate comprising albumin, a variant or fragment thereof. The albumin may be a serum albumin, such as human serum albumin, obtained from an animal or from a microorganism such as a yeast.

BACKGROUND OF THE INVENTION

Albumin is used to treat patients with severe burns, shock or blood loss. It is also used to supplement media used for growing higher eukaryotic cells and as an excipient for pharmacologically active compounds, many of which need to be stabilised. Albumin fusion proteins are a fusion of a protein to albumin, or to a variant or fragment thereof, and increases the half life of the protein, for example increased in vivo half life. At present albumin is obtained from blood products, such as serum, or produced recombinantly in microogranisms such as yeast or from transgenic plants or animals. The albumin must be purified from the production source in order to provide a product which is sufficiently pure to meet the user's needs and/or to achieve a high yield of product.

A problem with current albumin products is the purification process required. High purity can be achieved but this requires multiple chromatographic purification steps which can be time consuming and/or expensive. For example, the purification process described in WO 2000/044772 comprises a three-step process: cation exchange chromatography followed by anion exchange chromatography followed by dye-binding (affinity) chromatography. Therefore, what is required is a simpler purification process.

SUMMARY OF THE INVENTION

The invention provides a simpler purification process for albumin. Thus the invention relates to a process for purifying albumin, a variant or fragment thereof, a fusion protein comprising albumin, a variant or fragment thereof, or a conjugate comprising albumin, a variant or fragment thereof, the process comprising:
(i) loading a solid matrix comprising an albumin specific ligand bound to a solid support with an aqueous solution comprising albumin, a variant or fragment thereof, a fusion protein comprising albumin, a variant or fragment thereof, or a conjugate comprising albumin, a variant or fragment thereof;
(ii) washing the matrix to remove at least some impurities; and
(iii) eluting the albumin, a variant or fragment thereof, a fusion protein comprising albumin, a variant or fragment thereof, or a conjugate comprising albumin, a variant or fragment thereof from the matrix to provide a purified albumin, a variant or fragment thereof, a fusion protein comprising albumin, a variant or fragment thereof, or a conjugate comprising albumin, a variant or fragment thereof.

The inventors have identified that well known separation steps, previously used in purification of albumins, such as cation exchange and dye binding processes; can be replaced by a single affinity process which increases clearance of undesired proteins relative to such steps and/or increases the yield.

Throughout this specification, the term 'albumin' includes naturally occurring albumin, albumin-related proteins and variants thereof such as natural and engineered variants. Variants include polymorphisms, fragments such as domains and sub-domains, fragments and/or fusion proteins. The albumin may have at least 40, 50, 60, 70, 80, 90, 95, 96, 97, 98, 99% similarity or identity to SEQ ID No. 1.

| Lane | Sample | Load |
|---|---|---|
| 1. | rHA | 1 μg |
| 2. | Load | 1/100 |
| 3. | Load | 1/1000 |
| 4. | Flow Through | nt. |
| 5. | Wash 1 | nt. |
| 6. | Wash 2 | nt. |
| 7. | Wash 3 | nt. |
| 8. | Wash 4 | nt. |
| 9. | Eluate | 1/1000 |
| 10. | rHA | 1 μg |

Figure 2:
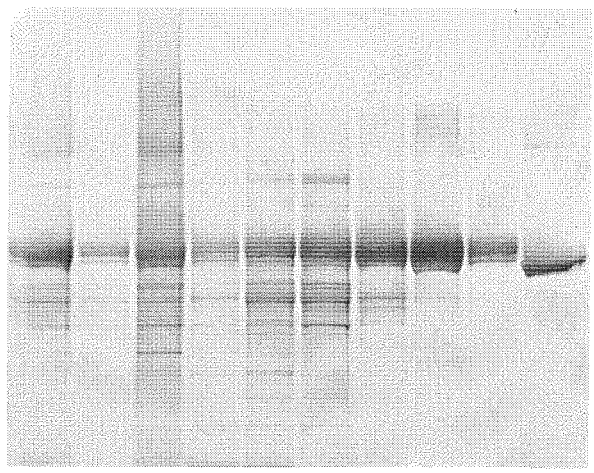

FIG. 2 shows SDS-PAGE of T20 albumin fusion purification, see example 2

| Lane | Sample | Load |
|---|---|---|
| 1. | Load | 1/100 |
| 2. | Load | 1/1000 |
| 3. | Flow Through | Nt |
| 4. | Wash 1 | Nt |
| 5. | Wash 2 | Nt |
| 6. | Wash 3 | Nt |
| 7. | Wash 4 | Nt |
| 8. | Eluate | 1/100 |
| 9. | Eluate | 1/1000 |
| 10. | rHA | 1 μg |

Figure 3:
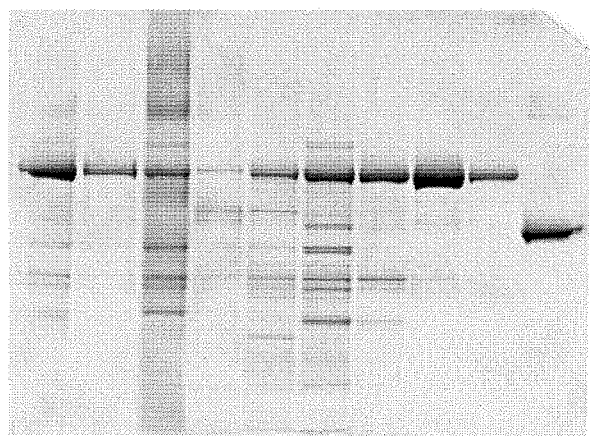

FIG. 3 shows SDS-PAGE of IL1RA Albumin fusion purification, see example 2.

| Lane | Sample | Load |
|---|---|---|
| 1. | Load | 1/100 |
| 2. | Load | 1/1000 |
| 3. | Flow Through | nt |
| 4. | Wash 1 | nt |
| 5. | Wash 2 | nt |

-continued

| Lane | Sample | Load |
|---|---|---|
| 6. | Wash 3 | nt |
| 7. | Wash 4 | nt |
| 8. | Eluate | 1/100 |
| 9. | Eluate | 1/1000 |
| 10. | rHA | 1 µg |

Figure 4:
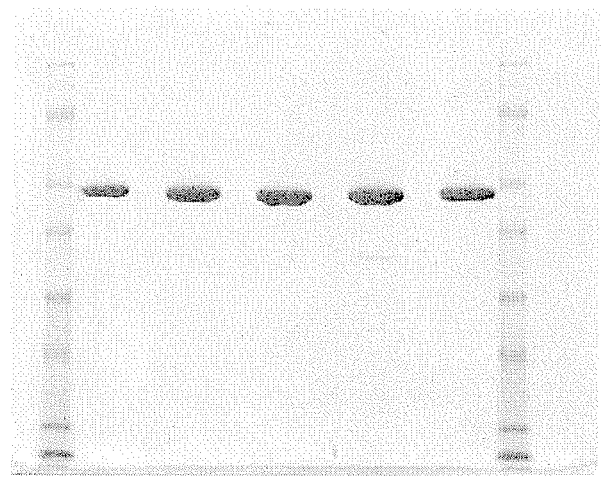

FIG. 4 shows SDS-PAGE of AlbuPure™ Purified Animal Albumins, see example 8:

| 1BLane | 2BSample | 3BLoad |
|---|---|---|
| 1 | SeeBlue ® Plus2 MW standard | 5 µL |
| 2 | Rabbit Serum Albumin | 2 µg |
| 3 | Mouse Serum Albumin | 2 µg |
| 4 | Rat Serum Albumin | 2 µg |
| 5 | Dog Serum Albumin | 2 µg |
| 6 | Human Serum Albumin | 2 µg |
| 7 | SeeBlue ® Plus2 MW standard | 5 µL |

Figure 5:
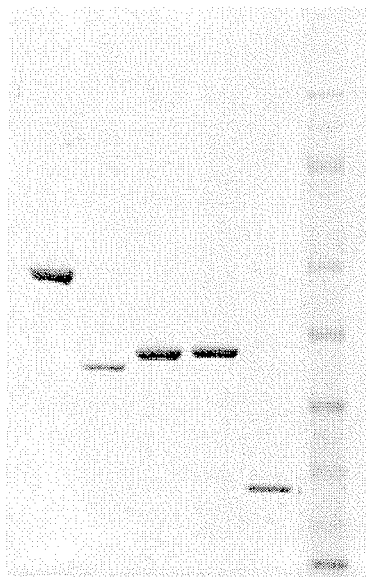

FIG. 5 shows. SDS-PAGE of AlbuPure™ Purified Albumin Fragmentsm see example 8:

| Lane | Sample | Load |
|---|---|---|
| 1 | HSA | 1 µg |
| 2 | Human Serum Albumin Domain 1 + 2 | 1 µg |
| 3 | Human Serum Albumin Domain 2 + 3 | 1 µg |
| 4 | Human Serum Albumin Domain 1 + 3 | 1 µg |
| 5 | Human Serum Albumin Domain 3 | 1 µg |
| 6 | SeeBlue ® Plus2 MW standard | 5 µL |

DETAILED DESCRIPTION OF THE INVENTION

The present invention relates to a process for purifying albumin, a variant or fragment thereof, a fusion protein comprising albumin, a variant or fragment thereof, or a conjugate comprising albumin, a variant or fragment thereof. The term purifying is in this application and claims intended to mean a procedure by which at least one undesired compound, such as cell debris, other plasma or host cell proteins, salts, lipids carbohydrates etc. is reduced relative to the desired compound. Depending on the starting material for the process; the undesired compound is completely or partially removed from the desired compound, albumin, a variant or fragment thereof or a fusion protein comprising albumin, a variant or fragment thereof.

Albumin is known in the area as the most abundant protein of plasma and it has been described and characterized from a large number of mammals and birds, where it is believed to have a role in keeping the correct osmotic pressure and it also has a role in transport of various compounds in the blood stream.

The process of the invention may in principle be used for purifying any known albumin such as albumin derived from human beings, dog, sheep, goat, bovine, cow, donkey, rabbit, mouse, rat, hamster, guinea pig and chicken. A preferred albumin is human serum albumin in particular human serum albumin having the sequence disclosed in SEQ ID NO: 1.

Variants of albumin is according to the invention intended to mean compounds having the overall structure of albumin but which has been altered in at least one amino acid residue compared with the parent albumin. In this connection the parent albumin is understood as the natural not altered albumin compound. The variant may differ in more than one position from the parent albumin, and in principle there is no well defined upper limit for the number of alterations, including substitutions, deletions or insertions of amino acid residues as well as chemical modifications; as long as the variant maintains the overall structure of albumin. In a preferred embodiment the albumin variant comprises one alteration, preferably at least 2 alterations, more preferred at least 5 alterations, more preferred at least 10 alterations, even more preferred at least 20 alterations and most preferred at least 25 alterations compared with the parent albumin.

The variant albumin has preferably at least 60% sequence identity to the parent albumin, preferably at least 70% sequence identity, more preferred at least 80% sequence identity, even more preferred at least 90% sequence identity, even more preferred at least 95% sequence identity and most preferred at least 98% sequence identity to the parent albumin.

In a preferred embodiment the albumin, fragment or variant thereof has at least 40, 50, 60, 70, 80, 90, 95, 96, 97, 98, 99% sequence identity to SEQ ID No. 1.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

In describing the various variants of the present invention, the nomenclature described below is adapted for ease of reference. In all cases, the accepted IUPAC single letter or triple letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent: | Variant: |
|---------|----------|
| 195     | 195 195a 195b |
| G       | G-K-A    |

In a preferred embodiment the variant albumin is derived from human serum albumin having the sequence shown in SEQ ID NO: 1, by substitution, deletion or insertion of at least 1 amino acid residue, preferably at least 2 amino acid residues, more preferred at least 5 amino acid residues, even more preferred at least 10 amino acid residues.

In another preferred embodiment the variant albumin is made of hybrid albumin comprising a part derived from human serum albumin and a part derived from another albumin.

As examples of variant albumins can be mentioned the natural variant having lower plasma half-life disclosed in (*Biochim Biophys Acta.* 1991, 1097:49-54) having the substitution D494N. Preferred albumin variants includes variants generated in albumin in order to provide a reactive thiol group on the surface such as the variants of SEQ ID NO: 1: L585C, D1C, A2C, D562C, A364C, A504C, E505C, T79C, E86C, D129C, D549C, A581C, D121C, E82C, S270C, A578C, L595LC, D1DC, A2AC, D562DC, A364AC, A504AC, E505EC, T79TC, E86EC, D129DC, D549DC, A581AC, A581AC, D121DC, E82EC, S270SC, A579AC, 0360*, 0316*, 075*, C168*, 0558*, 0361*, C91*, 0124*, 0169* and 0567*, described in the unpublished PCT application PCT/EP2010/051751, included herein by reference; and the variants of SEQ ID NO: 1 altered in positions 492, 493, 494, 495, and 496, disclosed in the unpublished EP patent application EP09174698.2, included herein by reference.

A fragment of albumin is intended to be understood as a molecule comprising part of an albumin molecule but wherein at least another part of the albumin molecule is absent. The fragment may comprise the N- or C-terminal part of albumin or an internal part of albumin and it may even be composed of two or more albumin fragments that are not directly connected in the natural albumin molecule. As example of preferred albumin fragments are the domain I, domain II and domain III; as well as combinations of two of these. The term fragments of albumin encompass also fragments of albumin variants.

A fragment of albumin may even comprise one or more parts of one albumin and one or more parts of one or more different albumins, e.g. a part of human serum albumin and another part of rabbit serum albumin.

A fragment of albumin comprises at least of 10 amino acid residues, preferably at least 25 amino acid residues, more preferred at least 50 amino acid residues, even more preferred at least 100 amino acid residues, more preferred at least 200 amino acid residues, more preferred at least 300 amino acid residues, more preferred at least 400 amino acid residues, and most preferred at least 500 amino acid residues.

The term 'fusion protein' comprising albumin, a variant or fragment thereof is according to the invention intended to mean a polypeptide comprising sequences of albumin, a variant or fragment thereof and further one or more sequences that are distinct from albumin, a variant or fragment thereof.

The non-albumin part(s) of the fusion protein may in principle be any polypeptide, however, it is preferred that it has a medical use.

The fusion protein may or may not have a linker sequence between the albumin part(s) and the non-albumin part(s), which linker may contain a cleavage site for a specific protease.

In a preferred embodiment the non-albumin part of the fusion protein is a polypeptide having a medical use, e.g. a polypeptide having a therapeutic use.

As examples of fusion proteins can be mentioned the albumin fusion polypeptides disclosed in the WO 9315199, WO 01079271 and WO 03059934, incorporated herein by reference.

A conjugate comprising albumin, a variant or fragment thereof is according to the invention intended to mean a compound prepared by chemically attaching one or more conjugation partners to comprising albumin, a variant or fragment thereof. The conjugation partner may be a bioactive compound such as a therapeutic or diagnostic compound. The therapeutic compound may be a chemotherapy drug for use in cancer chemotherapy. It may be cytostatic or cytotoxic; it may be a tumor-inhibiting agent.

The conjugation partner may be attached to the albumin, a variant or fragment thereof using methods known as such in the art.

Examples of suitable conjugation partners and methods for joining the conjugation partner and the albumin, a variant or fragment thereof can be found in WO 2009019314 and in the unpublished EP patent application EP09174698.2, both documents incorporated herein by reference.

The first step in the claimed method is providing a solid matrix comprising an albumin specific ligand bound to a solid support. The solid matrix comprising an albumin specific ligand bound to a solid support has the ability to specifically bind albumin. Such matrices having the ability to bind a specific protein with a higher affinity than other compounds are known in the art.

The albumin specific ligand may in principle be any ligand having a high affinity to albumin. A ligand specific for albumin may in principle be found by binding candidate ligands to a solid support, testing the affinity by contacting the candidate ligands with an albumin solution, rinsing the ligands with an albumin free solution and subsequent evaluating the candidate ligands ability to bind albumin by the amount of albumin attached to the candidate ligands after the rinse.

A preferred albumin specific ligand is 2-chloro-4,6-di-(2'-sulphoanilino)-S-triazine.

The solid support may in principle be any solid material that is inert under the contemplated conditions. By inert it is meant that the solid support does not take part or only in an insignificant degree take part in chemical interactions with components of the aqueous solution comprising albumin, the washing solutions and the elution solution.

Examples of solid supports that may be used according to the invention includes polymers such as cellulose or agarose and derivatives thereof, polyethylene, polystyrene, polyacrylate, and silicates.

Such solid supports and methods for binding the albumin specific ligand to the solid support are known in the art, and the skilled person will appreciate how to apply such teachings to the present invention. As example of a preferred method for binding the albumin specific ligand to the solid support can be found in WO 97/10887. (A particular preferred solid matrix comprising the albumin binding ligand 2-chloro-4,6-di-(2'-sulphoanilino)-S-triazine bound to a solid support is the solid matrix available under the tradename 'Albupure™' from ProMetic BioSciences Ltd, Cambridge, UK.

The solid matrix comprising the albumin binding ligand is usually packed as a fixed bed in a cartridge, a column or other form of container wherein the solid material can be packed and the aqueous solution comprising the albumin, a variant or fragment thereof, a fusion protein comprising albumin, a variant or fragment thereof, or a conjugate comprising albumin, a variant or fragment thereof, washing and elution solutions can flow through the fixed bed comprising the solid matrix, however, other well known techniques such as mixing the solid matrix with the appropriate solution in a container followed by a separation step e.g. filtration or centrifugation; and fluid bed technologies may also be applied to the process of the invention. Techniques for providing affinity materials such as the solid matrix comprising an albumin specific ligand is known in the art and it will be within the skills of the average practitioner to select and apply a suitable technique to the present invention.

The aqueous solution comprising albumin, a variant or fragment thereof, a fusion protein comprising albumin, a variant or fragment thereof, or a conjugate comprising albumin, a variant or fragment thereof may in principle be any such solution. Examples or suitable aqueous solutions comprising albumin, a variant or fragment thereof, a fusion protein comprising albumin, a variant or fragment thereof, or a conjugate comprising albumin, a variant or fragment thereof includes: plasma or fractions thereof, culture supernatants from a cell culture of a cell capable of producing such protein, milk of transgenic animals capable of producing such proteins and extracts of transgenic plants capable of producing such proteins. The aqueous solution comprising albumin, a variant or fragment thereof, a fusion protein comprising albumin, a variant or fragment thereof, or a conjugate comprising albumin, a variant or fragment thereof may be the medium wherein the protein is produced, e.g. a cell culture supernatant, or it may be a partially purified fraction thereof.

The pH of the aqueous solution comprising albumin, a variant or fragment thereof, a fusion protein comprising albumin, a variant or fragment thereof, or a conjugate comprising albumin, a variant or fragment thereof to be contacted with the solid matrix should have a pH in the range of 4-9.5 preferably, 4-9, more preferred 4-8, and most preferred 4.5-8. If the aqueous solution does not have such a pH by itself it is generally necessary to adjust the pH using well known pH regulating compounds e.g. sodium hydroxide or potassium hydroxide for increasing the pH and hydrochloric acid, sulphuric acid or acetic acid for reducing the pH.

The aqueous solution comprising albumin, a variant or fragment thereof, a fusion protein comprising albumin, a variant or fragment thereof, or a conjugate comprising albumin, a variant or fragment thereof is loaded on to the solid matrix comprising an albumin binding ligand using well known techniques. The skilled person will appreciate that loading conditions may be optimized taking into consideration factors such as loading amount, loading rate, flow velocity, contact time etc., and such optimization is well within the skills of the skilled person.

During the loading the aqueous solution comprising albumin, a variant or fragment thereof, a fusion protein comprising albumin, a variant or fragment thereof, or a conjugate comprising albumin, a variant or fragment thereof to the solid matrix the albumin, a variant or fragment thereof, a fusion protein comprising albumin, a variant or fragment thereof, or a conjugate comprising albumin, a variant or fragment thereof will bind to the albumin binding ligand connected to the solid matrix.

After loading the solid matrix comprising an albumin binding ligand, now bound to albumin, a variant or fragment thereof, a fusion protein comprising albumin, a variant or fragment thereof, or a conjugate comprising albumin, a variant or fragment thereof is washed to remove impurities.

In this connection impurities are intended to mean compounds other than albumin, a variant or fragment thereof, a fusion protein comprising albumin, a variant or fragment thereof, or a conjugate comprising albumin, a variant or fragment thereof contained in the aqueous solution comprising albumin, a variant or fragment thereof, a fusion protein comprising albumin, a variant or fragment thereof, or a conjugate comprising albumin, a variant or fragment thereof. The impurities may be compounds such as proteins, carbohydrates, lipids, small organic molecules, salts, chemical reagents etc., and usually a mixture of various different impurities will be present.

The matrix is washed with aqueous solutions generally composed of water, inorganic salts and buffer systems. Additional compounds such as surfactants, preservatives chelators may also be present. Generally washing solutions are known in the art and can be used according to the invention. In case that the solid matrix is placed in a fixed bed the washing steps are typically performed by perfusing the fixed bed with washing solution in a volume corresponding to at least 1 volume of the fixed bed, preferably at least 2 volumes, more preferred at least 3 volumes and most preferred at least 5 volumes of the fixed bed.

The washing solution may have a pH in the range of 4-9.5, more preferred 4-9, even more preferred 4-8, and most preferred 5-8.

The wash may be performed in one or more steps where the solid matrix in each step is washed with a washing solution.

It is preferred to use two or more washing steps, that may be performed using washing solutions having same pH or by using washing solutions having different pHs. In one preferred embodiment the pHs of the two or more washing steps are different and the pH of the two or more washing steps are consecutively rising or are consecutively declining, preferably the pH of the two or more washing steps are consecutively rising.

In the embodiment of two or more washing steps of consecutively rising pH the pH of the first washing step is preferably in the range of pH 4.0-8.0, preferably in the range of pH 4.0-7.0 more preferred in the range of pH4.0-6.0. The last washing step is preferably in the range of pH 7.0-9.5, preferably in the range of pH 8.0-9.5 and most preferred in the range of pH 8.5-9.5. Preferably there is at least one further step between the first and the last step such as 1, 2, 3, 4 or 5 steps between the first and the last step.

After the washing steps the albumin, a variant or fragment thereof, a fusion protein comprising albumin, a variant or fragment thereof, or a conjugate comprising albumin, a variant or fragment thereof is eluted from the solid matrix using an elution solution comprising a salt of an fatty acid, a thiocyanate salt, or by using a elution solution having a pH at 10.0 or higher or any combination thereof.

The salt of a fatty acid preferably a salt of a fatty acid having a solubility in the elution solution at the elution conditions of at least 10 mM, preferably at least 20 mM more preferred at least 50 mM, even more preferred at least 100 mM and most preferred at least 500 mM. As examples of suitable salts of fatty acids can be mentioned sodium and potassium salts of acetate, propanoate, butyrate, pentanoate, hexanoate, heptanoate, octanoate, nonanoate and decanoate.

The concentration of the salt of the fatty acid in the elution solution is preferably in the range of 5 mM to 0.5 M, preferably in the range of 10 mM to 100 mM.

In principle any thiocyanate may be used according to the invention, however, it is preferred to use a thiocyanate salt having a solubility in the elution solution at the elution conditions of at least 10 mM, preferably at least 20 mM more preferred at least 50 mM, even more preferred at least 100 mM, even more preferred at least 500 mM and most preferred at least 1 M. Further it is preferred to use a thiocyanate salt have a cation that is acceptable in the final product. Suitable examples of thiocyanate salts that may be used according to the invention includes: sodium thiocyanate and potassium thiocyanate. The thiocyanate salt is preferably used in the elution solution in a concentration in the range of 5 mM to 1M, preferably in the range of 10 mM to 500 mM.

The elution solution may further comprise buffer systems, salts and preserving agents, preferably of pharmaceutical grade. It will be within the skills of the average practitioner to compose the elution solution based on the teachings herein and the art of affinity matrices.

The elution is generally done in a small volume in order to obtain the albumin, a variant or fragment thereof, a fusion protein comprising albumin, a variant or fragment thereof, or a conjugate comprising albumin, a variant or fragment thereof in a high concentration, but on the other side it is desirable to use a larger volume in order to obtain a larger yield. The skilled person will therefore have to optimize the elution with respect to volume, flow rate etc., using well known methods for optimization.

According to the process of the invention a recovery of the albumin, a variant or fragment thereof, a fusion protein comprising albumin, a variant or fragment thereof, or a conjugate comprising albumin, a variant or fragment thereof is high, generally more than 25%, preferably more than 40%, more preferred more than 50%, more preferred more than 60%, even more preferred more than 70%, even more preferred more than 80% and most preferred more than 90%.

The process of the invention may be performed as a part of a longer purification procedure involving one or more additional purification steps before and/or after the process of the invention or it may be performed without additional steps. Generally, in particular where the solid matrix is provided in a fixed bed, it is preferred that a separation step is performed before the process of the invention in order to remove particulate material and/or lipid micelles from the aqueous solution comprising the albumin, a variant or fragment thereof, a fusion protein comprising albumin, a variant or fragment thereof, or a conjugate comprising albumin, a variant or fragment thereof, which particulate material and/or micelles otherwise might clog the fixed bed and deteriorate the flow properties of the bed.

The invention is now further described in the following examples which should not be considered limiting in any way.

EXAMPLES

Materials

Solid matrix: A solid matrix comprising the ligand 2-chloro-4,6-di-(2'-sulphoanilino)-S-triazine was used. This solid matrix is available under the tradename 'Albupure™' from ProMetic BioSciences Ltd, Cambridge, UK Recombinant human serum albumin (rHSA): The culture supernatant of a fermentation of a recombinant yeast comprising an expression plasmid encoding human serum albumin was used as a source of rHSA. Generation of the expression plasmid, transforming the yeast strain and fermentation conditions are essentially as disclosed in WO 00/44772 example 1.

Example 1

Comparison of rHSA 2 Step AlbuPure™ Purification and 3 Step Conventional Purification The conventional 3 step purification of cation ion exchange, anion exchange and dye affinity chromatography was performed as described in WO 2000/044772.

The 2 step AlbuPure™ purification was performed by conditioned the rHSA fermentation supernatant for chromatography using acetic acid and water to achieve a pH of approximately 5.3 and a conductivity of approximately 3 mS·cm$^{-1}$. A column packed with AlbuPure™ matrix was equilibrated with 50 mM sodium acetate pH 5.3. A volume of conditioned sample equivalent to 20 mg rHSA·mL$^{-1}$ matrix was loaded. The matrix was washed sequentially with 50 mM sodium acetate pH 5.3, 50 mM sodium phosphate pH 6.0, 50 mM sodium phosphate pH 7.0 and 50 mM ammonium acetate pH 8.0 before being eluted with 50 mM ammonium acetate, 10 mM sodium octanoate pH 7.0 and finally regenerated with 0.5M sodium hydroxide. The AlbuPure™ eluate was conditioned for anion ion exchange chromatography by diluting with water to 2.5 mS/cm and adjusting the pH with acetic acid to pH 5.5. The anion exchange chromatography was performed using DE-FF Sepharose as described in WO 2000/044772. The albumin yield was calculated from the concentration measured by GP-HPLC and related back to the total amount at the start. The host cell proteins (HCP) were measured by sandwich ELISA using anti yeast antibodies and measured as a fold clearance relative to the starting material.

TABLE 1

| Purification Step | 3 Step Process (WO 2000/044772) | | 2 Step Process (AlbuPure ™ & DE-FF) | |
|---|---|---|---|---|
| | Total rHA Yield (%) | HCP Clearance (Fold) | Total rHA Yield (%) | HCP Clearance (Fold) |
| Start | 100 | | 100 | |
| Step 1 Eluate | 49 | 104 | 70 | 1394 |
| Step 2 Eluate | 53 | 728 | 60 | 95619 |
| Step 3 Eluate | 42 | 99736 | | |

Consequently, the 2 step process gives 18% more yield (product) while maintaining approximately equivalent HCP levels (within the limits of the assay).

Example 2 rHSA Fusions

Figure 1:
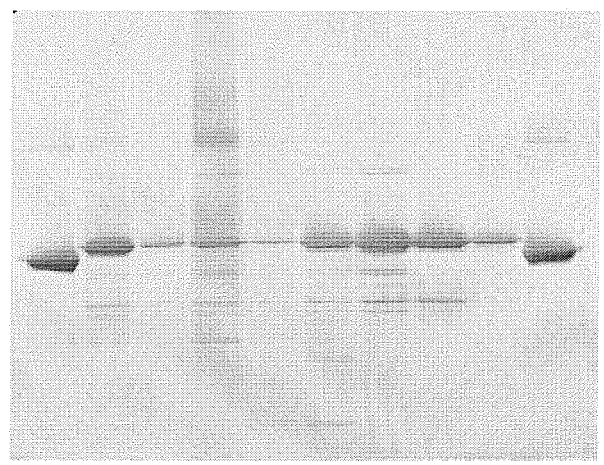
FIG. 1. SDS-PAGE of Prosaptide albumin fusion purification, see example 2.

Yeast derived culture supernatant containing c-terminal rHSA fusions of prosaptide, T20 (PCT/IB03/00434) and IL1RA were conditioned for chromatography using acetic acid and water to achieve a pH of approximately 5.3 and a conductivity of between 2.6 and 3.3 mS·cm$^{-1}$. A 1.6 cm×11.0 cm (22.1 mL) column packed with AlbuPure™ matrix was equilibrated with 50 mM sodium acetate pH 5.3. A volume of conditioned sample equivalent to 20 mg fusion protein·mL$^{-1}$ matrix was loaded. The matrix was washed sequentially with 50 mM sodium acetate pH 5.3, 50 mM sodium phosphate pH 6.0, 50 mM sodium phosphate pH 7.0 and 50 mM ammonium acetate pH 8.0 before being eluted with 50 mM ammonium acetate, 10 mM sodium octanoate pH 7.0 and finally regenerated with 0.5M sodium hydroxide. SDS_PAGE of Prosaptide albumin fusion purification is shown in FIG. 1. SDS-PAGE of T20 albumin fusion purification is shown in FIG. 2. SDS-PAGE of IL1RA Albumin fusion purification is shown in FIG. 3.

Example 3

Anti FITC (scFv(vHvL)-rHSA-FLAG) Antibody

Yeast derived culture supernatant containing the anti FITC (scFv(vHvL)-rHSA-FLAG) (disclosed in EP application No 09 159 642) antibody fusion (N-terminal fusion) was conditioned for chromatography using water to achieve a pH of 6.2 and a conductivity of 7.9 mS·cm$^{-1}$. A 4.4 cm×11.0 cm (167.3 mL) column packed with AlbuPure™ matrix was equilibrated with 50 mM sodium phosphate pH 6.0. A volume of conditioned sample equivalent to 9.5 mg protein·mL$^{-1}$ matrix was loaded. The matrix was washed sequentially with 50 mM sodium phosphate pH 6.0, 50 mM sodium phosphate pH 7.0 and 50 mM ammonium acetate pH 8.0. Bound protein was eluted first with 50 mM ammonium acetate, 10 mM sodium octanoate pH 7.0 and then with 50 mM ammonium acetate, 30 mM sodium octanoate, 200 mM sodium chloride pH7.0. The matrix was regenerated with 0.5M sodium hydroxide. A total of 84% of the anti FITC (scFv(vHvL)-rHSA-FLAG) was recovered in the 2 eluates combined, as estimated by GP.HPLC.

Example 4

Anti AMA (vNAR-rHSA-FLAG) Antibody Fusion

Yeast derived culture supernatant containing the anti AMA (vNAR-rHSA-FLAG) antibody fusion (N-terminal fusion) was purified without adjustment at a pH of 5.8 and a conductivity of 47.0 mS·cm$^{-1}$. A 2.6 cm×11.0 cm (58.4 mL) column packed with AlbuPure™ matrix was equilibrated with 50 mM sodium phosphate pH 6.0 and a volume of sample equivalent to 14.25 mg protein·mL$^{-1}$ matrix loaded. The matrix was washed first with 50 mM sodium phosphate pH 6.0 then 50 mM ammonium acetate pH 8.0. Bound protein was eluted first with 50 mM ammonium acetate, 10 mM sodium octanoate pH 7.0, then with 50 mM ammonium acetate, 30 mM sodium octanoate, 200 mM sodium chloride pH7.0 and finally with phosphate buffered saline containing 1M potassium thiocyanate pH 8.6. The matrix was regenerated with 0.5M sodium hydroxide. A total of 53% of the anti AMA (vNAR-rHSA-FLAG) was recovered in the 3 eluates combined, as estimated by GP.HPLC.

Example 5

Effect of Loading the AlbuPure Matrix in the pH Range 4.0-10.0

The effect on step recovery and matrix capacity of loading at pH 4.0, 5.0, 6.0, 6.5, 7.0, 7.5, 8.0, 8.5, 9.0, 9.5 and 10.0 was investigated. Load material was prepared by diluting partially purified N-terminal anti-FITC scFv-rHA fusion to 10 mg·mL$^{-1}$ with a buffer of the appropriate pH increment. The pH of each load sample was then checked and adjusted using sodium hydroxide or glacial acetic acid as necessary. A toll 5 mm dia.×10 mm bed height centrifugally driven MediaScout® MiniColumns containing 200 µL AlbuPure™ matrix (ProMetic Biosciences) were equilibrated with 1 mL 50 mM sodium acetate pH 5.0. Sufficient load material (1 mL) was applied to each column to achieve a 50 mg fusion protein·mL$^{-1}$ matrix loading. Each column was washed first with 1 mL 50 mM sodium acetate pH 5.0 (wash 1) and then 1 mL 50 mM ammonium acetate pH 8.0 (wash 2). Each column was then eluted with 1 mL 50 mM ammonium acetate, 50 mM sodium octanoate pH 8.0. All chromatographic fractions were collected and the scFv-rHA fusion concentration estimated by gel permeation high performance liquid chromatography (GP.HPLC). Recoveries and capacities were tabulated and are shown in Table 2. The recovery in this instance is calculated from the total amount bound to the column (amount in load minus amount in flow through) rather than the amount loaded to give a more representative result in this experiment. The capacity was calculated from the amount bound (amount in load minus amount in flow through) divided by the matrix volume (200 µL).

TABLE 2

The effect of load pH on scFv-rHA fusion recovery and AlbuPure matrix capacity

| Load conditions | Recovery (%) | | | | | Capacity (mg/mL matrix) |
|---|---|---|---|---|---|---|
| | Flow through | Wash 1 | Wash 2 | Eluate | Mass Balance | |
| pH 4.0 | 5.3 | 1.1 | 14.3 | 89.3 | 105.2 | 52.0 |
| pH 5.0 | 11.2 | 1.2 | 10.9 | 86.6 | 100.1 | 49.5 |
| pH 6.0 | 18.6 | 3.6 | 2.8 | 92.4 | 100.2 | 45.8 |
| pH 6.5 | 25.3 | 7.1 | 1.0 | 89.8 | 100.5 | 41.5 |
| pH 7.0 | 26.4 | 8.3 | 0.3 | 88.8 | 100.3 | 41.3 |
| pH 7.5 | 30.5 | 12.5 | 0.2 | 86.8 | 103.4 | 38.8 |
| pH 8.0 | 32.7 | 10.8 | 0.1 | 73.4 | 93 | 38.3 |
| pH 8.5 | 37.1 | 12.7 | 0.1 | 75.7 | 97.5 | 35.0 |
| pH 9.0 | 43.0 | 15.9 | 0.0 | 69.5 | 98.5 | 31.7 |
| pH 9.5 | 45.6 | 17.1 | 0.0 | 58.3 | 94.4 | 30.0 |
| pH 10.0 | 72.1 | 18.7 | 0.0 | 31.8 | 99.7 | 15.9 |

Data indicates that a range of 4.0-9.5 for loading pH is suitable.

Example 6

Effect of Different Washing pH Combinations

The effect on step recovery and yeast antigen (YA) clearance of washing with combinations of buffers at different pH increments was investigated. Load material was prepared by thawing and filtering (0.8 µm) frozen N-terminal anti-FITC scFv-rHA fusion fermentation culture supernatant. No further conditioning was performed. A toll 5 mm dia.×10 mm bed height centrifugally driven MediaScout® MiniColumns containing 200 µL AlbuPure™ matrix (ProMetic Biosciences) were equilibrated with 1 mL 50 mM sodium acetate pH 5.0. Sufficient load material (1 mL) was applied to each column to achieve a 20 mg fusion protein·mL$^{-1}$ matrix loading. Each column was washed as shown in Table 2. Each column was then eluted with 1 mL 50 mM ammonium acetate, 50 mM sodium octanoate pH 8.0. All chromatographic fractions were collected and the scFv-rHA fusion concentration estimated by gel permeation high performance liquid chromatography (GP.HPLC). YA levels were estimated by enzyme linked immunosorbent assay (ELISA). Recoveries and YA clearance were tabulated and are shown in Table 3. The YA clearances are normalized back to the full wash regime (pH 5, 6, 7 & 8), as used in Example 1.

TABLE 3

The effect of different combinations of washing pH on scFv-rHA fusion recovery

| Wash conditions | Recovery (%) | | | | | | | |
|---|---|---|---|---|---|---|---|---|
| | Flow through | Wash 1 | Wash 2 | Wash 3 | Wash 4 | Eluate | Mass Balance | YA Clearance |
| pH 5, 6, 7 & 8 | 5.2 | 0.7 | 0.2 | 6.0 | 4.5 | 87.9 | 104.5 | 1.00 |
| pH 5 & 4 | 9.0 | 1.0 | 0.2 | N/A | N/A | 51.0 | 61.2 | 1.36 |
| pH 5 & 5 | 9.8 | 1.0 | 0.2 | N/A | N/A | 84.3 | 95.2 | 0.40 |
| pH 5 & 6 | 11.0 | 1.4 | 0.5 | N/A | N/A | 88.1 | 101.0 | 0.15 |
| pH 5 & 7 | 7.6 | 1.0 | 6.0 | N/A | N/A | 87.6 | 102.1 | 0.40 |
| pH 5 & 8 | 5.2 | 0.7 | 7.1 | N/A | N/A | 91.0 | 104.0 | 0.33 |
| pH 5 & 9 | 8.1 | 1.0 | 32.9 | N/A | N/A | 63.8 | 105.7 | 0.78 |
| pH 5 & 10 | 11.0 | 1.0 | 76.9 | N/A | N/A | 13.1 | 101.9 | 0.67 |
| pH 8, 7, 6 & 5 | 10.2 | 10. | 2.4 | 0.0 | 0.0 | 81.0 | 103.6 | 3.94 |
| pH 4, 7, & 10 | 10.5 | 1.0 | 5.7 | 66.4 | N/A | 18.6 | 102.1 | 1.29 |
| pH 10, 7, & 4 | 10.0 | 89.5 | 1.4 | 0.0 | N/A | 0.0 | 101.0 | N/A |
| pH 8 & 5 | 10.0 | 10.5 | 2.1 | N/A | N/A | 73.1 | 95.7 | 2.00 |
| pH 4 & 10 | 9.5 | 0.1 | 82.9 | N/A | N/A | 11.2 | 103.7 | 0.76 |
| pH 10 & 4 | 12.4 | 87.4 | 1.7 | N/A | N/A | 0.0 | 101.4 | N/A |
| pH 4 | 9.5 | 1.0 | N/A | N/A | N/A | 41.4 | 51.9 | 0.37 |
| pH 8 | 10.2 | 11.0 | N/A | N/A | N/A | 88.3 | 109.5 | 0.28 |

Data indicates that wash conditions between pH 5 and pH 9, to be performed in any order to give recoveries and/or yeast antigen (HCP) clearances better than cation exchanges as per Example 1. At pH 10 material is prematurely eluted, as shown below pH 4 also works but care is required with the elution if pH 4 is the last wash prior to elution.

| Wash conditions | Recovery (%) | | | | | | |
|---|---|---|---|---|---|---|---|
| | Flow through | Wash 1 | Wash 2 | Wash 3 | Wash 4 | Eluate | Mass Balance |
| pH 4 & 8 | 3.0 | 0.8 | 8.6 | N/A | N/A | 82.1 | 94.5 |

Example 7

Effect of Different Elution Conditions

The effect on step recovery for various eluents was investigated. Load material was prepared by diluting partially purified N-terminal anti-FITC scFv-rHA fusion to 4 mg·mL$^{-1}$ with 50 mM sodium acetate pH 5.0. Atoll 5 mm dia.×10 mm bed height centrifugally driven MediaScout® MiniColumns containing 200 μL AlbuPure™ matrix (ProMetic Biosciences) were equilibrated with 1 mL 50 mM sodium acetate pH 5.0. Sufficient load material (1 mL) was applied to each column to achieve a 20 mg fusion protein·mL$^{-1}$ matrix loading. Each column was washed first with 1 mL 50 mM sodium acetate pH 5.0 (wash 1) and then 1 mL 50 mM ammonium acetate pH 8.0 (wash 2). Each column was then eluted with the appropriate buffer (Table 3). All chromatographic fractions were collected and the scFv-rHA fusion concentration estimated by gel permeation high performance liquid chromatography (GP.HPLC). Recoveries were tabulated and are shown in Table 4.

TABLE 4

The effect of different eluents on scFv-rHA fusion recovery

| Elution conditions | Recovery (%) | | | | |
|---|---|---|---|---|---|
| | Flow through | Wash 1 | Wash 2 | Eluate | Mass Balance |
| 50 mM ammonium acetate, 50 mM sodium octanoate pH 6.0 | 0.5 | 0.0 | 6.0 | 84.2 | 90.6 |
| 50 mM ammonium acetate, 50 mM sodium octanoate pH 7.0 | 2.2 | 0.0 | 7.2 | 88.2 | 97.6 |
| 50 mM ammonium acetate, 50 mM sodium octanoate pH 8.0 | 2.6 | 0.2 | 6.5 | 90.4 | 99.8 |
| 2M sodium octanoate pH 8.2 | 4.8 | 0.5 | 7.4 | 25.7 | 38.4 |
| 100 mM sodium octanoate pH 8.0 | 0.2 | 0.0 | 5.0 | 95.4 | 100.7 |
| 0.5M octanoate pH 10 | 0.0 | 0.0 | 4.0 | 56.2 | 60.1 |
| 1M octanoate pH 10 | 0.0 | 0.0 | 6.4 | 26.2 | 36.3 |
| 50 mM ammonium acetate 500 mM sodium propionate pH 8.0 | | | | 26 | |
| 50 mM ammonium acetate 500 mM sodium butyrate pH 8.0 | | | | 56 | |
| 50 mM ammonium acetate 500 mM sodium hexanoate pH 8.0 | | | | 86 | |

TABLE 4-continued

The effect of different eluents on scFv-rHA fusion recovery

| Elution conditions | Recovery (%) | | | | |
|---|---|---|---|---|---|
| | Flow through | Wash 1 | Wash 2 | Eluate | Mass Balance |
| PBS, 0.5M potassium thiocyanate pH 7.0 | 0.5 | 0.0 | 5.3 | 104.6 | 110.3 |
| PBS, 1M potassium thiocyanate pH 7.0 | 0.2 | 0.0 | 6.2 | 93.0 | 99.5 |
| PBS, 0.5M sodium thiocyanate pH 7.0 | 1.9 | 0.2 | 7.2 | 86.1 | 95.4 |
| PBS, 1M sodium thiocyanate pH 7.0 | 0.5 | 0.0 | 6.0 | 94.0 | 100.5 |
| 50 mM sodium carbonate pH 10 | 0.0 | 0.0 | 2.0 | 66.3 | 68.3 |
| 50 mM glycine pH 10 | 0.0 | 0.0 | 2.9 | 58.6 | 61.5 |
| 50 mM sodium phosphate pH 10 | 0.0 | 0.0 | 2.6 | 62.6 | 65.2 |
| 50 mM ammonium acetate pH 10.0 | 2.4 | 0.2 | 6.7 | 71.0 | 80.3 |
| 50 mM potassium tetraborate pH 10.0 | 0.5 | 0.0 | 6.5 | 28.1 | 35.0 |

Example 8

Albumin Fragments and Animal Albumins

Animal albumins and albumin fragments were purified from shake flask culture supernatant using a single chromatographic step using AlbuPure™ matrix. Culture supernatant (350 mL) was applied to a 6 cm bed height, 2.0 mL packed bed equilibrated with 50 mM sodium acetate pH5.3. Following loading, the column was washed with 50 mM sodium acetate pH5.3 then 50 mM ammonium acetate pH8.0. Product was eluted with either 50 mM ammonium acetate 10 mM octanoate pH8.0, 50 mM Ammonium Acetate 30 mM Sodium Octanoate 200 mM Sodium Chloride pH7.0 or 200 mM Potassium thiocyanate. The column cleaned with 0.5M NaOH. SDS-PAGE of AlbuPure™ Purified Animal Albumins: is shown in FIG. 4.

The invention claimed is:

1. A process for purifying albumin, a variant or fragment thereof, a fusion protein comprising albumin, a variant or fragment thereof, or a conjugate comprising albumin, a variant or fragment thereof the process comprising:
   (i) loading a solid matrix comprising 2 chloro-4,6-di(2'-sulphoanilino)-S-triazine bound to a solid support with an aqueous solution comprising albumin, a variant or fragment thereof, a fusion protein comprising albumin, a variant or fragment thereof, or a conjugate comprising albumin, a variant or fragment thereof;
   (ii) washing the matrix to remove at least some impurities; and
   (iii) eluting the albumin, an albumin, a variant or fragment thereof, a fusion protein comprising albumin, a variant or fragment thereof, or a conjugate comprising albumin, a variant or fragment thereof from the matrix to provide a purified albumin, a variant or fragment thereof, a fusion protein comprising albumin, a variant or fragment thereof, or a conjugate comprising albumin, a variant or fragment thereof, wherein the albumin, variant or fragment thereof, fusion protein comprising albumin, variant or fragment thereof, or conjugate comprising albumin, a variant or fragment thereof comprises a sequence having at least 90% sequence identity to SEQ ID NO: 1.

2. The process according to claim 1 where the albumin is derived from a mammal, human, rabbit, mouse, goat, sheep, cow; or bird.

3. The process according to claim 1 in which the albumin, a variant or fragment thereof, a fusion protein comprising albumin, a variant or fragment thereof, or a conjugate comprising albumin, a variant or fragment thereof comprises a sequence having at least 95% sequence identity to SEQ ID NO: 1.

4. The process of claim 1, wherein the aqueous solution comprising albumin, a variant or fragment thereof, a fusion protein comprising albumin, a variant or fragment thereof, or a conjugate comprising albumin, a variant or fragment thereof is selected from a fermentation supernatant, a partially purified fermentation supernatant, serum, a serum fraction or a partially purified serum or serum fraction, milk from transgenic feedstock or extract form transgenic plants.

5. The process of claim 1, wherein the aqueous solution comprising albumin, a variant or fragment thereof, a fusion protein comprising albumin, a variant or fragment thereof, or a conjugate comprising albumin, a variant or fragment thereof being loaded on the matrix has a pH in the range of 4-9.5.

6. The process of claim 1, wherein the washing is made by one or more washes having a consecutive rising pH.

7. The process of claim 6, wherein the first wash has a pH in the range of 4.0 to 6.0.

8. The process of claim 6, wherein the last wash has a pH in the range of 7.0 to 9.0.

9. The process of claim 6, having at least one additional washing step.

10. The process of claim 1, wherein the albumin, a variant or fragment thereof, a fusion protein comprising albumin, a variant or fragment thereof, or a conjugate comprising albumin, a variant or fragment thereof is eluted from the matrix using an aqueous solution comprising a salt of a fatty acid or thiocyanate salt or eluted at pH 10 or higher.

11. The process of claim 10, wherein the salt of the fatty acid has a solubility in water of more than 10 mM.

12. The process of claim 11, wherein the fatty acid salt is selected from salts of butyrate, pentanoate, hexanoate, heptanoate, octanoate, nonanoate and decanoate.

13. The process of claim 10, wherein the concentration of the fatty acid salt in the elution buffer is in the range of 5 mM to 0.5M.

14. The process of claim 10, wherein the thiocyanate salt is selected among sodium, potassium, ammonium, barium or other Group 1 or 2 alkali metals.

15. The process of claim 10, wherein the thiocyanate salt is used in a concentration in the range of 5 mM to 1M.

16. The process of claim 10, wherein the concentration of the fatty acid salt in the elution buffer is in the range of 10 mM to 100 mM.

17. The process of claim 10, wherein the thiocyanate salt is used in a concentration in the range of 10 mM to 500 mM.

* * * * *